United States Patent [19]

Speight, II et al.

[11] Patent Number: 5,372,043
[45] Date of Patent: Dec. 13, 1994

[54] METHOD AND APPARATUS FOR ULTRASONIC INSPECTION OF CURVED NACELLE COMPONENTS

[75] Inventors: John W. Speight, II; Fred M. Burns, both of Fort Worth; Thomas J. Blackstock, Alvarado; Donald S. Lotz, Arlington, all of Tex.

[73] Assignee: Vought Aircraft Company, Dallas, Tex.

[21] Appl. No.: 932,109

[22] Filed: Aug. 19, 1992

[51] Int. Cl.$^5$ .............................. G01N 9/24
[52] U.S. Cl. .................... 73/619; 73/640; 73/641; 73/633
[58] Field of Search ............ 73/583, 600, 618, 619, 73/633, 635, 640, 641, 644

[56] References Cited

U.S. PATENT DOCUMENTS

| | | | |
|---|---|---|---|
| 4,018,082 | 4/1977 | Manoliu et al. | 73/600 |
| 4,304,133 | 1/1981 | Feamster, III | 73/633 |
| 4,562,737 | 1/1986 | Davies | 73/633 X |
| 4,685,966 | 8/1987 | Garner et al. | 73/583 |

*Primary Examiner*—Richard E. Chilcot, Jr.
*Assistant Examiner*—Joseph L. Felber
*Attorney, Agent, or Firm*—Richards, Medlock & Andrews

[57] ABSTRACT

Ultrasonic inspection of composite products such as curved components of airplane engine nacelles utilizes guide wheels and rollers to support and control the nacelle component or panel and permit rotation of the nacelle panel about its longitudinal axis. The nacelle panel is passed through an inspection zone which contains an ultrasonic inspection assembly comprising ultrasonic transmitting transducers and ultrasonic receiving transducers mounted on opposite sides of the nacelle panel. The ultrasonic inspection assembly is mounted to be moved along a frame by a drive assembly whereby the ultrasonic inspection assembly is translated across the width of the nacelle panel. The nacelle panel is rotated about its axis in small incremental rotational steps by a cable driven by a motor drive assembly. After each incremental rotational movement of the nacelle panel, the ultrasonic inspection assembly is translated across the width of the nacelle panel to inspect the portion aligned with the frame. The entire nacelle is thus inspected as it is rotated through the ultrasonic inspection assembly.

35 Claims, 8 Drawing Sheets

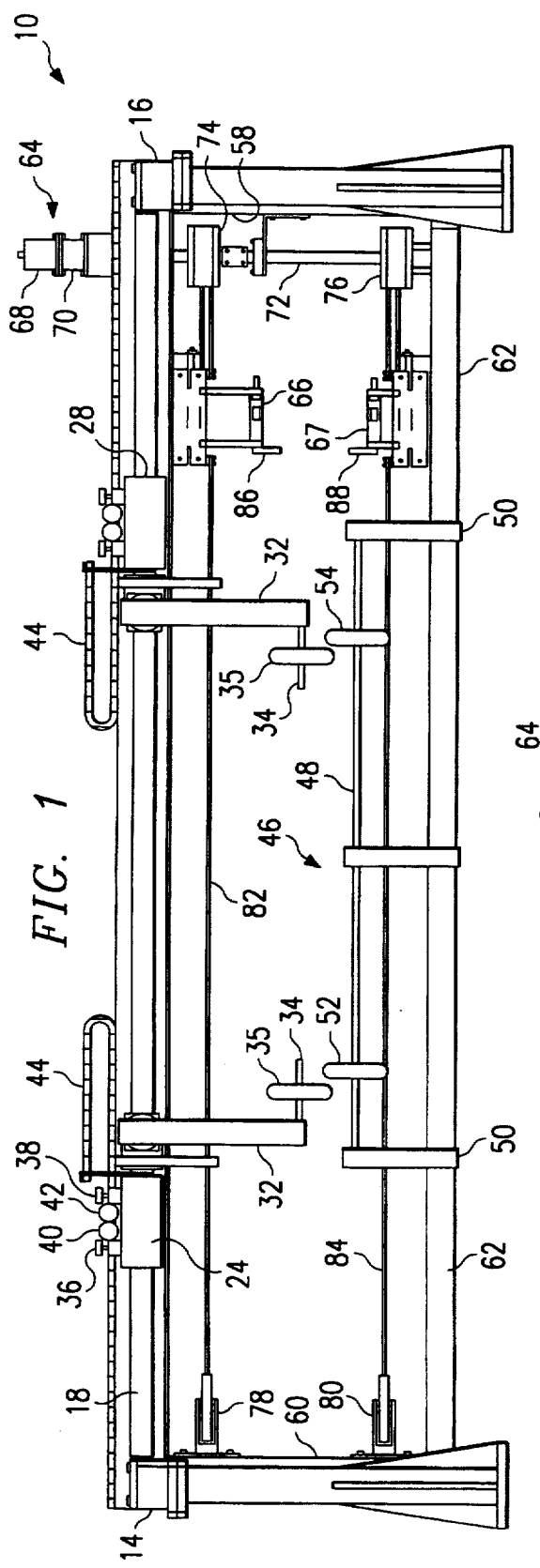
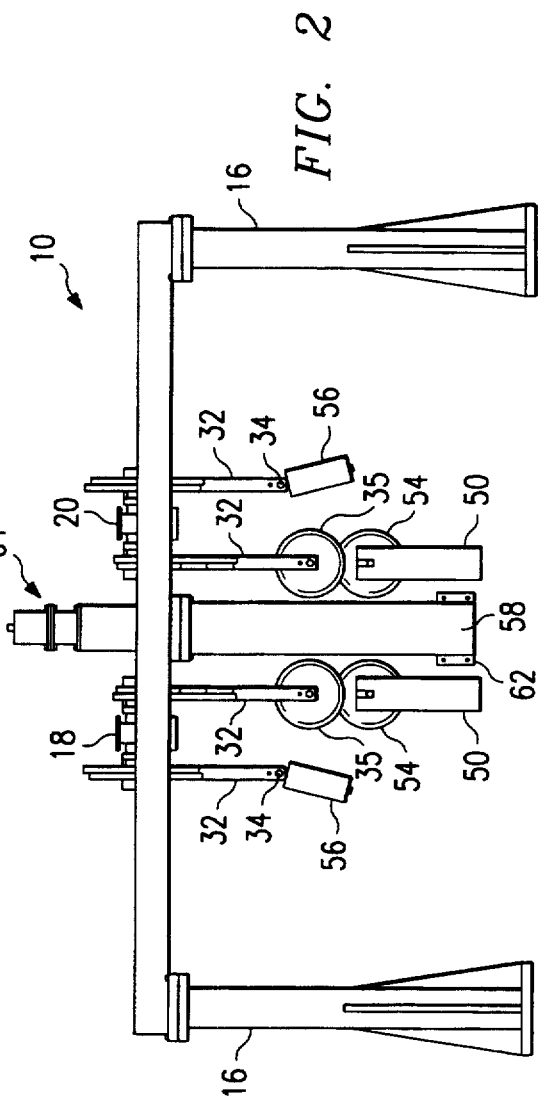

METHOD AND APPARATUS FOR ULTRASONIC INSPECTION OF CURVED NACELLE COMPONENTS

TECHNICAL FIELD OF THE INVENTION

This invention relates generally to ultrasonic inspection of components. More particularly, but not by way of limitation, this invention relates to ultrasonic inspection of curved composite panel products to determine the existence and location of any structural defects therein.

BACKGROUND OF THE INVENTION

Although this invention is applicable to the ultrasonic inspection of various types of composite products, it has been found to be particularly useful in the environment of ultrasonic inspection of the curved components or panels or airplane engine nacelles. Therefore, without admitting the applicability of the invention to "curved components of airplane engine nacelles", the invention will be described in such environment.

It is well known to use ultrasonic inspection to determine the existence and location of any structure defects in curved composite components and/or products and to display the results on the screen of a cathode ray tube. Heretofore, it has been necessary to have a full compound contoured scanning system or to scan the composite component in predetermined zones using inspection equipment designed for planar inspection applications. These two methods require either expensive and complicated equipment or long periods of time to run the testing, which results in either a large capital investment or an expensive test period. In the past, many stiffened nacelle panels required multiple scans to perform an inspection of a nacelle panel. The web area of the stiffened nacelle panel can be inspected with the ultrasonic transducers oriented at generally ninety degrees to the web area while the stiffened areas must be run with the ultrasonic transducers oriented at an angle other than normal with respect to the web area.

The present invention provides apparatus which moves the nacelle panel through an ultrasonic inspection zone while maintaining control of the panel to always provide a nearly horizontal orientation of the surface of the nacelle panel at the inspection zone as the panel is moved through the ultrasonic inspection zone. The panel is scanned ninety degrees to the direction in which the panel is moved through the ultrasonic inspection zone. The test time using the apparatus of the present invention is approximately one-tenth the time needed when using the prior art rectilinear apparatus.

SUMMARY OF THE INVENTION

This invention provides a method and apparatus for the ultrasonic inspection of composite products such as curved components or panels of airplane engine nacelles. The apparatus comprises guide wheels and rollers to support and control the nacelle component or panel and permit indexing of the nacelle panel about its longitudinal axis. The nacelle panel is passed through an inspection zone. Ultrasonic transmitting transducers and ultrasonic receiving transducers are mounted on opposite sides of the nacelle panel to inspect the nacelle panel as the panel is moved through the inspection zone. The nacelle panel is indexed about its axis in small incremental rotational steps through the inspection zone by a cable drive assembly. After each incremental rotational movement of the nacelle panel, the ultrasonic transmitting and receiving transducers are scanned across the width of the nacelle panel to inspect the portion of the panel within the inspection zone. The entire nacelle is thus inspected as it is indexed through the inspection zone.

In one aspect, the present invention provides a system for ultrasonic inspection of a nacelle panel which moves the nacelle panel through an inspection zone by pulling the nacelle panel through the inspection zone by the use of cables removably attached to the nacelle panel.

In another aspect, instead of trying to control the orientation of the ultrasonic transducers to maintain normality of the transducers to the surface of the nacelle panel by either setting up small rectilinear scan zones or by use of some sort of contour control mechanism, the nacelle panel is controlled by applied force from wheels to maintain the nacelle panel nearly horizontal in alignment while the nacelle panel is being scanned within the inspection zone.

In still another aspect, the semi-automated system can not only index the nacelle panel through the inspection zone but by the use of shaped wheels the system can walk along external tabs of the nacelle panel and still maintain control of the movement of the nacelle panel.

BRIEF DESCRIPTION OF THE DRAWINGS

Other advantages and features of the invention will become more apparent with reference to the following detailed description of a presently preferred embodiment thereof in connection with the accompanying drawings, wherein like reference numerals have been applied to like elements, in which:

FIG. 1 is a simplified front elevational view of a portion of the ultrasonic inspection system constructed in accordance with the present invention;

FIG. 2 is a simplified end elevational view of a portion of the ultrasonic inspection system constructed in accordance with the present invention;

DETAILED DESCRIPTION

Figure 3:
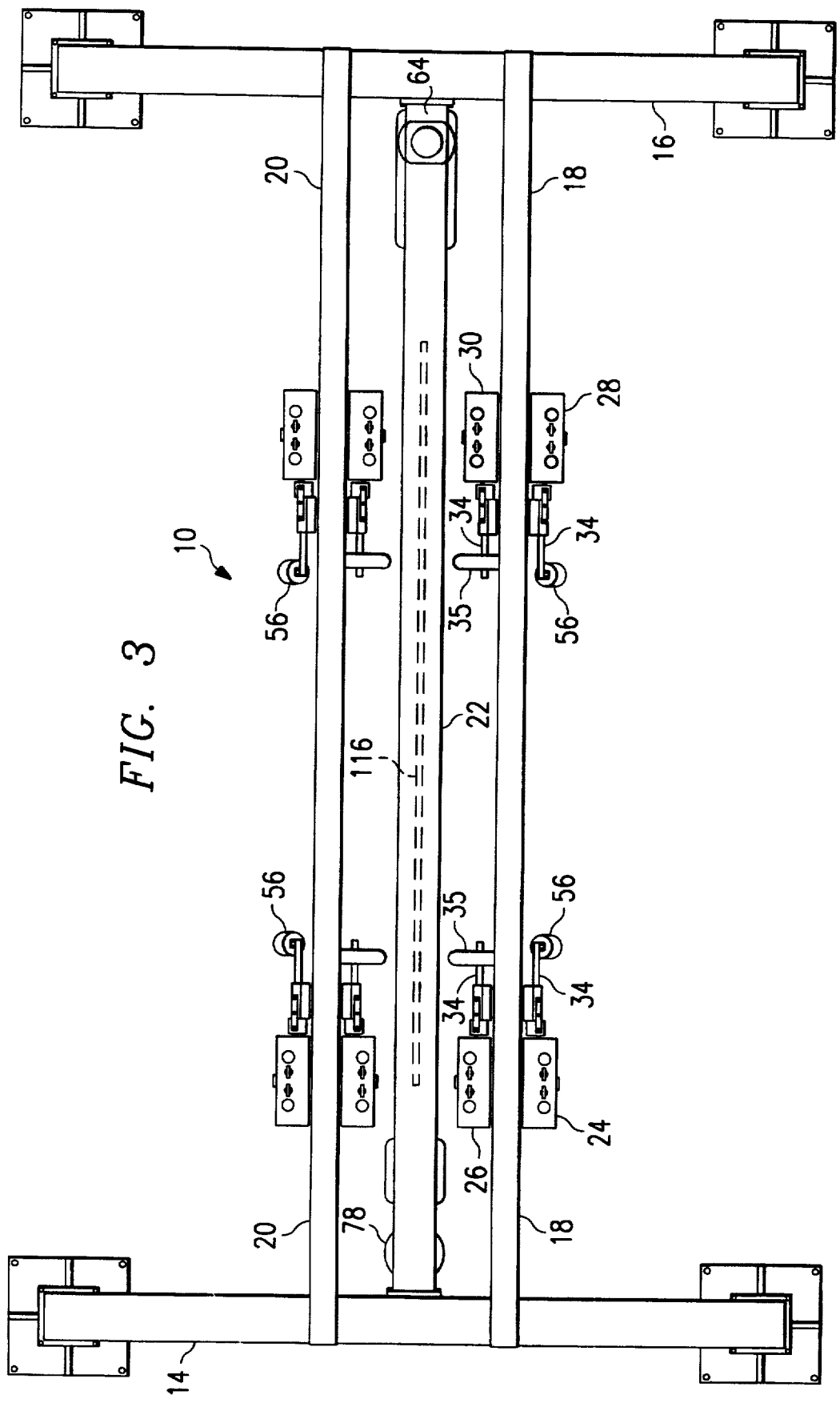
FIG. 3 is a simplified top plan view of a portion of the ultrasonic inspection system constructed in accordance with the present invention.

Referring to the drawings and FIGS. 1-3 in particular, shown therein and generally designated by the reference character 10 is a semi-automated system for the ultrasonic inspection of curved components that is constructed in accordance with the present invention. As illustrated, semi-automated system 10 comprises a first end frame assembly 14 and a second end frame assembly 16 which are positioned generally parallel to each other. First end frame assembly 14 and second end frame assembly 16 are connected by first upper frame 18 and second upper frame 20 which are parallel to each other and displaced from each other a predetermined distance and are generally perpendicular to the end frame assemblies 14 and 16. A central upper frame 22 is positioned between first upper frame 18 and second upper frame 20 and is also attached to the first end frame assembly 14 and second end frame assembly 16.

The wheel carriage assemblies supported by first upper frame 18 and second upper frame 20 for moving the nacelle panel through the inspection zone are identical in function; therefore, only the wheel carriage assembly supported by first upper frame 18 will be described to avoid redundancy. First wheel carriage assembly 24 and second wheel carriage assembly 26 are supported on the outer side and the inner side, respectively, of first upper frame 18 for movement along the length thereof. Third wheel carriage assembly 28 and fourth wheel carriage assembly 30 are supported on the outer side and the inner side, respectively, of first upper frame 18 for movement along the length thereof. Since each of the wheel carriage assemblies is identical in function, only first wheel carriage assembly 24 will be described to avoid redundancy. First wheel carriage assembly 24 comprises an arm 32 extending downwardly therefrom with a shaft 34 extending at generally right angles therefrom supporting upper wheel 35 which provides a rolling force to the upper surface of the nacelle panel during testing of the nacelle panel. Arm 32 is movable in a downward direction and an inward direction (toward third wheel carriage assembly 28). The movement of arm 32 is controlled by air pressure supplied through lines 44 and applied by valves 36 and 38. Pressure gauges 40 and 42 provide an indication to the operator of the air pressure.

Figure 4:
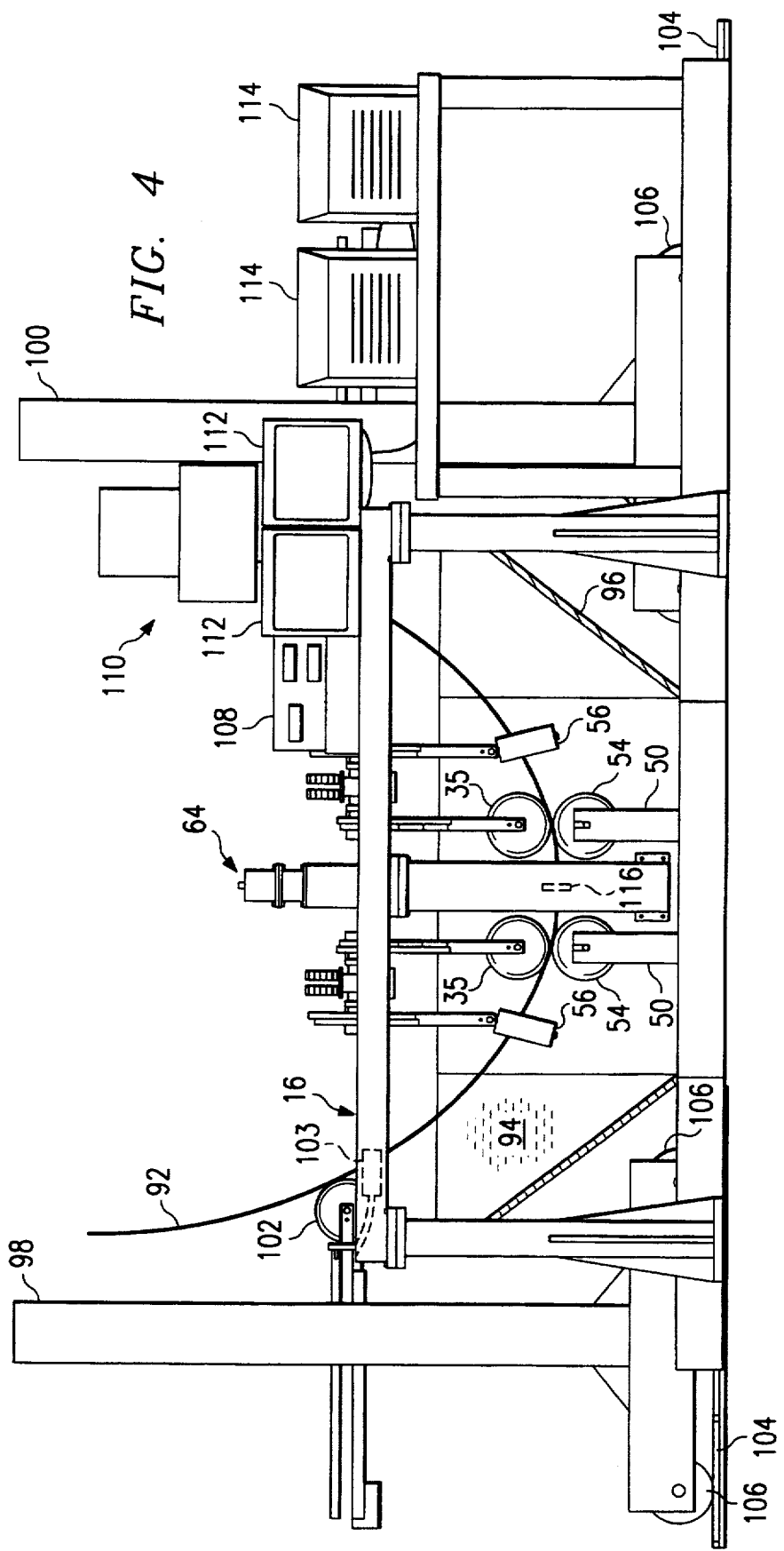
FIG. 4 is a simplified end elevational view of the ultrasonic inspection system constructed in accordance with the present invention, with the immersion tank in cross section.

Positioned below and in general alignment with first upper frame 18 is first lower wheel support assembly 46 including a shaft 48 supported by end supports 50. Lower wheels 52 and 54 are rotatably supported on shaft 48 and are positioned generally below upper wheels 35 associated with the inner wheel carriage assemblies 26 and 30, as shown in FIGS. 1, 2, and 4. Lower wheels 52 and 54 provide rolling support to the lower surface of the nacelle panel during testing. A second lower wheel support assembly, which is generally the same as first lower wheel support assembly 46, is positioned below and in general alignment with the inner wheel carriage assemblies which are mounted on the second upper frame 20, and provides support to the lower surface of the nacelle panel during testing.

With further reference to FIG. 2, some of the upper wheels 35 may be replaced by an edge roller 56 to supply a force against the edge of the nacelle panel 92 during the movement of the nacelle panel 92 through the inspection zone 116.

First upright support 58 extends downwardly from the central portion of second end frame assembly 16 and second upright support 60 extends downwardly from the central portion of first end frame assembly 14. Central lower frame 62 is operatively connected between first and second upright supports 58 and 60. Drive assembly 64 is mounted on central upper frame 22 and extends between the central upper frame 22 and the central lower frame 62 and moves upper and lower transducer carriages 66 and 67 along a predetermined path between the first and second end frame assemblies 14 and 16.

With reference to FIG. 1, drive assembly 64 comprises a stepper motor and any suitable electronic position feedback device 68, such as an encoder, mounted to gear assembly 70 to rotate shaft 72. Attached to shaft 72 is first upper pulley 74 and first lower pulley 76. Second upper pulley 78 is attached to second upright support 60 and in general alignment with first upper pulley 74 while second lower pulley 80 is attached to second upright support 60 in general alignment with first lower pulley 76. Upper belt or cable 82 is operatively coupled to and between first upper pulley 74, second upper pulley 78 and upper transducer carriage 66. Lower belt or cable 84 is operatively coupled to and between first lower pulley 76, second lower pulley 80 and lower transducer carriage 67.

With further reference to FIG. 1, upper transducer carriage 66 is structured to be supported by and to move back and forth along central upper frame 22 while lower transducer carriage 67 is structured to be supported by and to move back and forth along central lower frame 62. Upper transducer carriage 66 includes an ultrasonic transmitting transducer assembly 86 while lower transducer carriage 67 includes an ultrasonic receiving transducer assembly 88.

Figure 5:
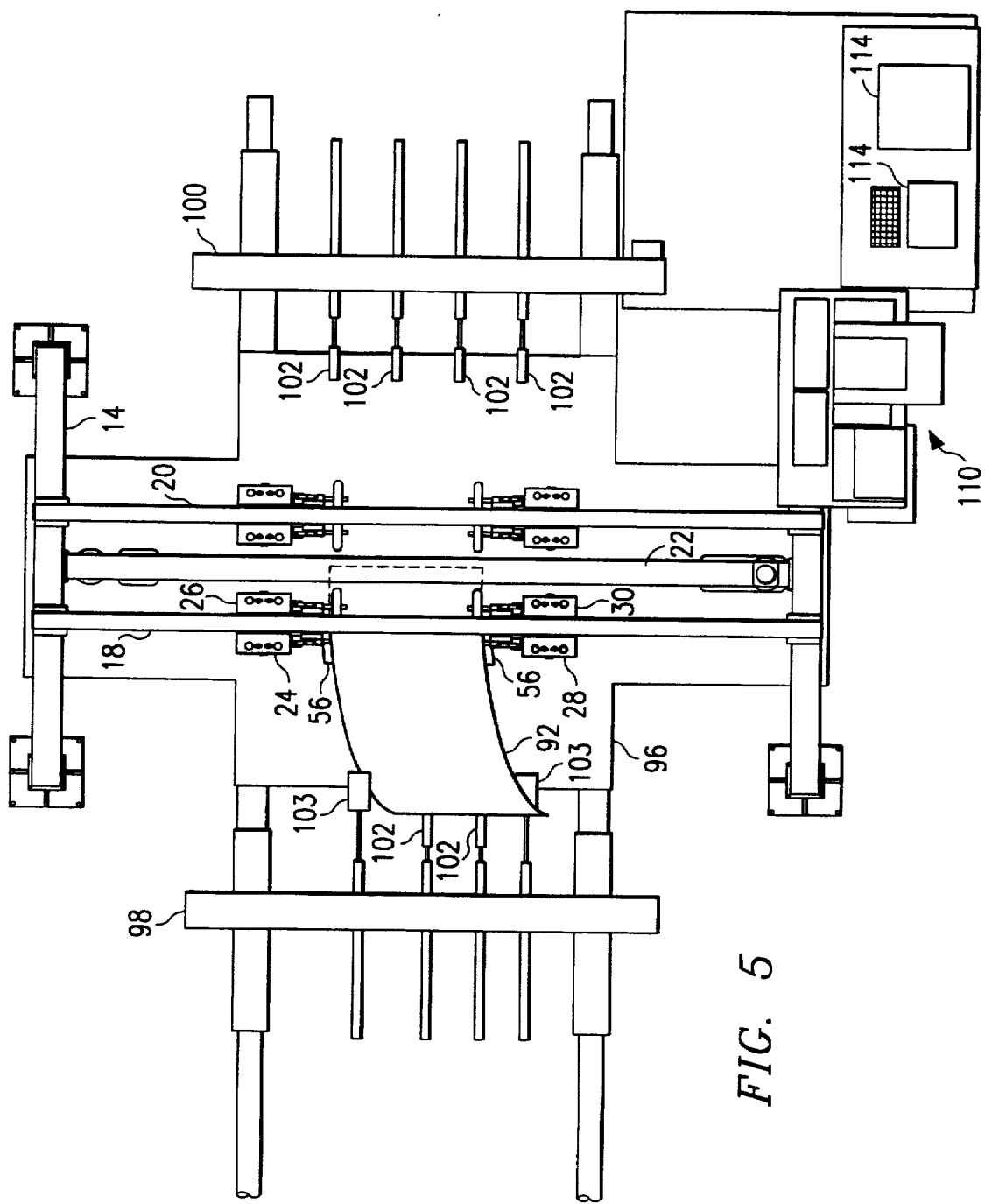
FIG. 5 is a simplified top plan view of the ultrasonic inspection system constructed in accordance with the present invention.

FIGS. 4 and 5 illustrate one embodiment of the semi-automated system 10 for the ultrasonic inspection of the curved components of airplane engine nacelles. Nacelle panel 92 is shown in operative position to be inspected and is being supported by wheels 35, 52, 54, and edge rollers 56 which are immersed in liquid medium 94, such as water, in tank 96. The ultrasonic transmitting and receiving transducer assemblies 86 and 88 are also immersed in water 94. First side stand 98 and second side stand 100, which are identical, are positioned on opposite sides of tank 96 and include wheels 102 which support the upper portions of nacelle panel 92 and rollers 103 which are positioned against the edges of nacelle panel 92. First and second side stands 98 and 100 are movable along tracks 104 on wheels 106 so the proper support may be provided to nacelle panel 92 by wheels 102 and rollers 103. Pressure source and controller 108 is operatively connected to valves 36 and 38. Programmable controller 110 provides the programmed instructions to drive assembly 64 to move upper and lower transducer carriages 66 and 67 during the inspection of nacelle panel 92. The signals received from the ultrasonic receiving transducer assembly 88 as the nacelle panel 92 is moved through the inspection zone 116 are displayed on the video displays 112 and are sent to recorders 114 where a permanent record is provided. The drive assembly to move the nacelle panel 92 is not shown in FIGS. 4 and 5 but is shown in FIGS. 8 and 9.

Figure 6:
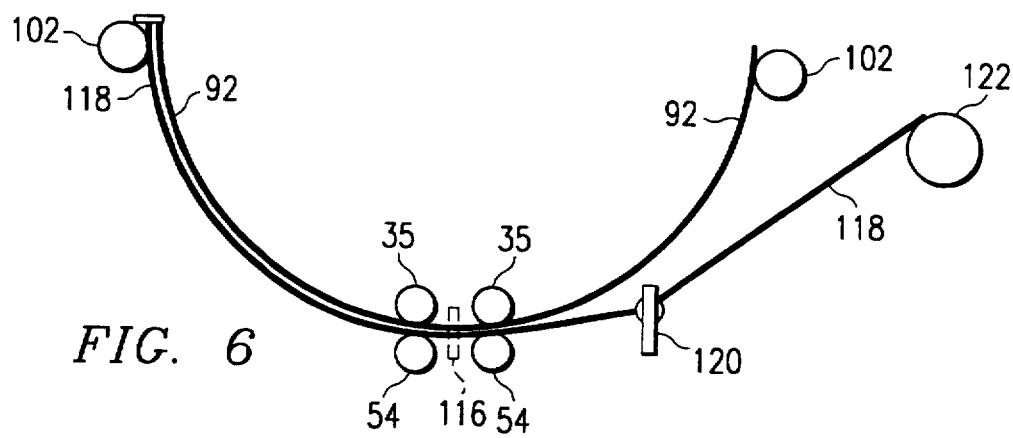
FIG. 6 is a simplified pictorial of the apparatus for moving the composite part through the inspection zone of the present invention.

With reference to FIG. 6, the concept of the apparatus to move the nacelle panel 92 through the inspection zone is illustrated. Nacelle panel 92 is supported by wheels 102, 35 and 54 as it is moved through the inspection zone 116. Wheels 35 and 54 maintain a preset force on the nacelle panel 92, due to the force maintained by the regulated air pressure, irrespective of the contour and/or shape of the nacelle panel 92. The portion of the nacelle panel 92 in the inspection zone 116 is maintained in a nearly horizontal configuration during the scanning by the ultrasonic transmitting and receiving transducer assemblies 86 and 88. At least one cable 118 is removably attached to the edge of nacelle panel 92 and is positioned along the underside of nacelle panel 92 and between lower wheels 52 and 54 and through wire guide 120 to drive assembly 122. A drive assembly is positioned on each side of tank 96 so the nacelle panel 92 can be pulled in either direction through the inspection zone 116 in tank 96. As illustrated in FIG. 8, each cable retainer assembly 156 can be provided with two cables 118.

Figure 7:
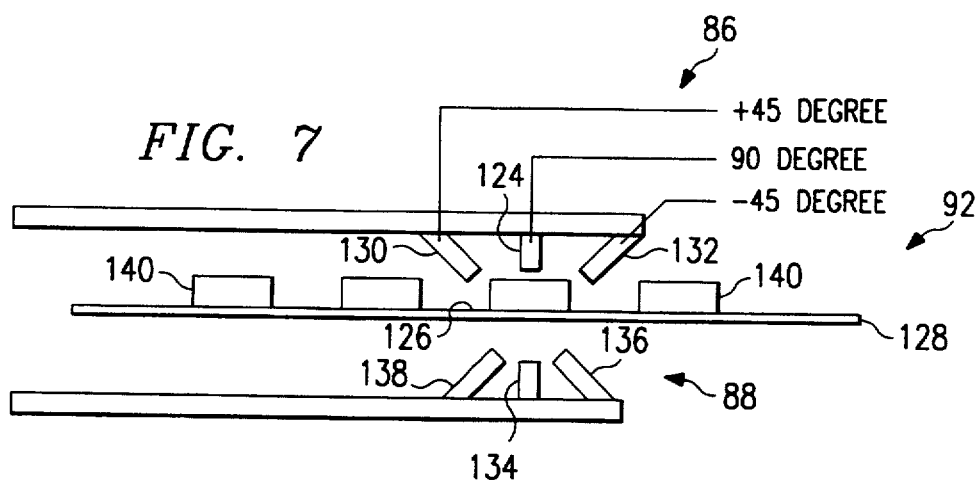
FIG. 7 is a simplified pictorial of the relative location of the ultrasonic transducers with respect to the composite part as the composite part moves through the inspection zone of the present invention.

FIG. 7 illustrates the individual transducers comprising the ultrasonic transmitting and receiving transducer assemblies 86 and 88. Ultrasonic transmitting transducer assembly 86 comprises a first transmitting transducer 124 which is oriented at generally ninety degrees with respect to the flat portion 126 of the web portion 128 of the nacelle panel 92. A second transmitting transducer 130 is oriented at generally plus forty-five degrees with respect to flat portion 126. In the preferred embodiment, second transmitting transducer 130 is oriented between plus forty degrees and plus fifty degrees depending upon the particular stiffened area 140. A third transmitting transducer 132 is oriented at generally minus forty-five degrees with respect to the flat portion 126. In the preferred embodiment, third transmitting transducer 132 is oriented between minus forty degrees and minus fifty degrees depending upon the particular stiffened area 140. Ultrasonic receiving transducer assembly 88 comprises a first receiving transducer 134 which is oriented at generally ninety degrees with respect to the flat portion 126 to receive the transmitted signal from first transmitting transducer 124. A second receiving transducer 136 is oriented at generally plus forty-five degrees with respect to flat portion 126 to receive the transmitted signal from second transmitting transducer 130. In the preferred embodiment, second receiving transducer 136 is oriented between plus forty degrees and plus fifty degrees depending upon the particular stiffened area 140 and the orientation of second transmitting transducer 130. A third receiving transducer 138 is oriented at generally minus forty-five degrees with respect to the flat portion 126 to receive the transmitted signal from third transmitting transducer 132. In the preferred embodiment, third receiving transducer 138 is oriented between minus forty degrees and minus fifty degrees depending upon the particular stiffened area 140 and the orientation of third transmitting transducer 132. The four transmitting and receiving transducers which are oriented at generally forty-five degrees provide for inspection of the vertical sides of stiffened areas 140 of the nacelle panel 92 at the same time the two transmitting and receiving transducers 124 and 134 are providing the inspection of the flat area of the stiffened areas 140 and the flat areas of the web portion 128. The present invention allows the stiffened areas 140 and the web portion 128 to be inspected with one set up and thereby greatly reduces the inspection time.

Figure 8:
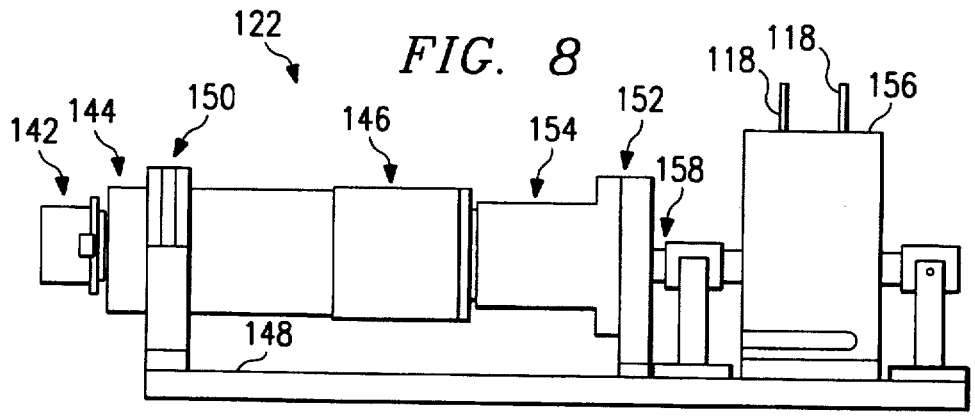
FIG. 8 is a simplified side elevational view of the apparatus for moving the composite part through the inspection zone of the present invention.
Figure 9:
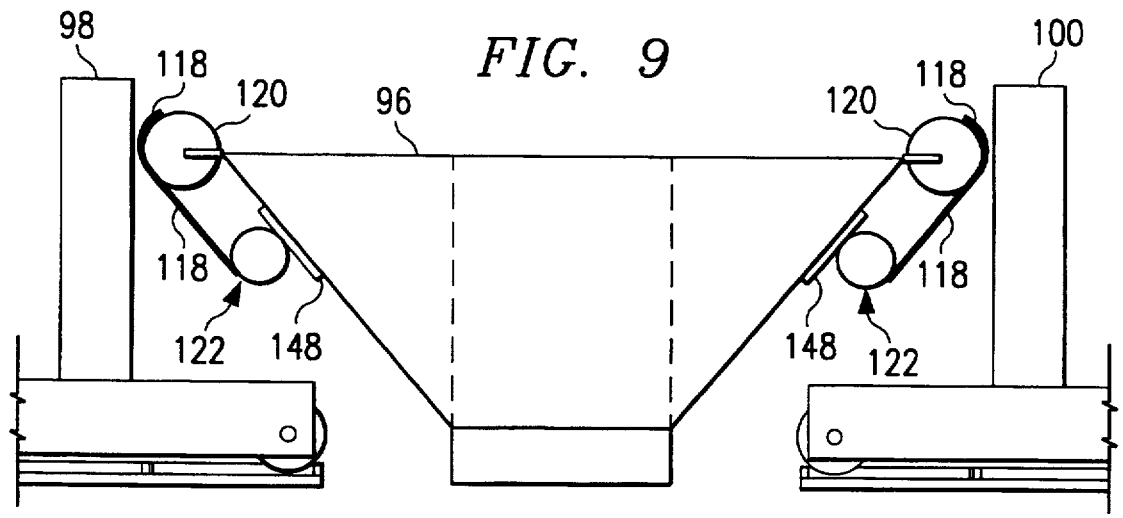
FIG. 9 is a simplified side elevational view of the apparatus for moving the composite part and the relation to the immersion tank of the present invention.

With reference to FIG. 8, drive assembly 122 comprises any suitable electronic position feedback device 142, such as an encoder, operatively coupled to stepper motor 144. Stepper motor 144 is operatively coupled to gear assembly 146 and is mounted to mounting frame 148 by mounting bracket 150. Gear assembly 146 is mounted to mounting bracket 152 by insulator mount 154. Cable retainer assembly 156 is driven by gear assembly 146 through drive shaft 158. Drive assembly 122 is driven and controlled by programmable controller 110 (FIG. 4). Mounting frame 148 is mounted to the side of tank 96 (FIG. 5).

With reference to FIG. 9, a drive assembly 122 is mounted at a predetermined position on each side of tank 96. Cables 118 extend from drive assembly 122, around wire guide 120, along the underside of nacelle panel 92 and on to the edge of nacelle panel 92 (see FIG. 6). With a drive assembly 122 mounted to each side of tank 96 and cables 118 removably attached to each end of nacelle panel 92, nacelle panel 92 can be pulled back and forth through the inspection zone 116 as determined by the programmable controller 110. Nacelle panel 92 is pulled through the inspection zone 116 by the cables 118 of drive assemblies 122.

It will be appreciated that the liquid medium needed to be present to provide the path through which the ultrasound travels from the transmitting transducer to the nacelle panel and from the nacelle panel to the receiving transducer can be provided by at least two different methods or techniques. One method or technique is by immersing or submerging the transducers and the nacelle panel in the liquid medium as shown in FIGS. 4 AND 5.

Figure 10:
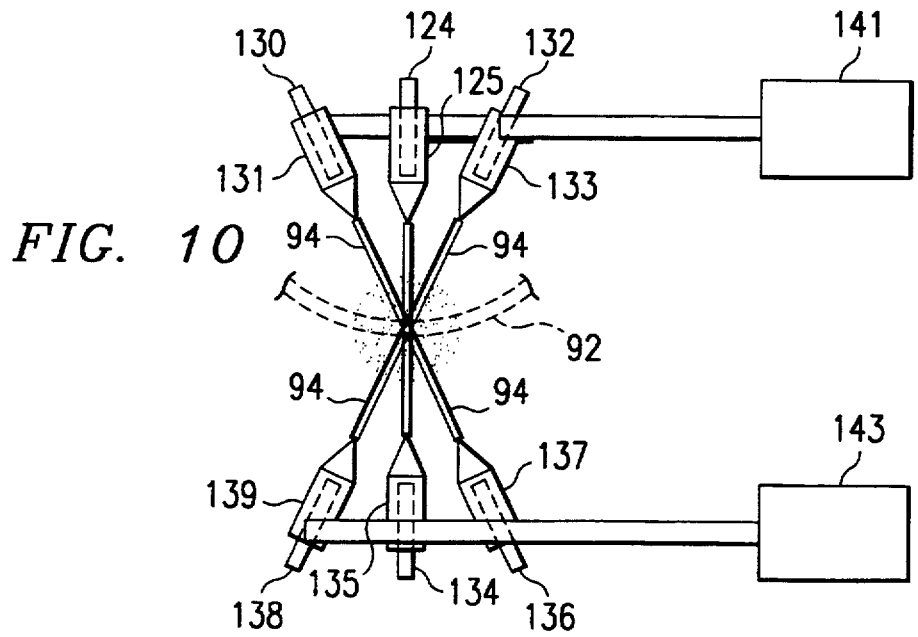
FIG. 10 is a simplified pictorial of apparatus for providing a stream of liquid medium from the transducers to the composite part.

FIG. 10 illustrates another method or technique which includes the provision of a stream or column of liquid medium between the transmitting transducer and the nacelle panel and between the receiving transducer and the nacelle panel. Each transmitting transducer 124, 130 and 132 is surrounded by an ejecting or squirting element or apparatus 125, 131 and 133, respectively. Liquid medium 94 is supplied under pressure to each ejecting or squirting element or apparatus 125, 131 and 133 by pressure system 141. Liquid medium 94 in the form of a continuous column is established between each of the transmitting transducers and the upper surface of nacelle panel 92.

Each receiving transducer 134, 136 and 138 is also surrounded by an ejecting or squirting element or apparatus 135, 137 and 139, respectively. Liquid medium 94 is supplied under pressure to each ejecting or squirting element or apparatus 135, 137 and 139 by pressure system 143. It will be appreciated that pressure systems 141 and 143 could be one and the same system. Liquid medium 94 in the form of a continuous column is established between each of the receiving transducers and the lower surface of nacelle panel 92.

Figure 11:
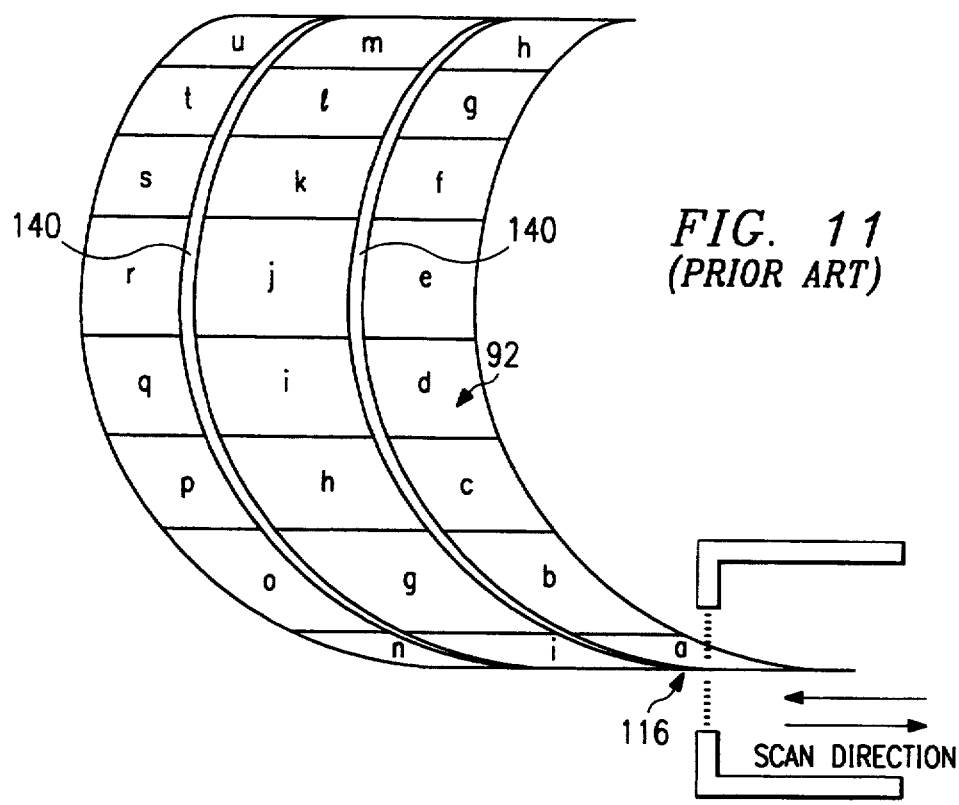
FIG. 11 is a simplified pictorial of the scanning zones of the prior art method of inspection.

FIG. 11 illustrates the prior art method of inspecting a nacelle panel 92. The nacelle panel 92 is scanned in individual zones, e.g. starting with zone a. After inspecting zone a, the system is then set up to inspect zone b, etc. with a separate set up necessary for each zone from a to u.

Figure 12:
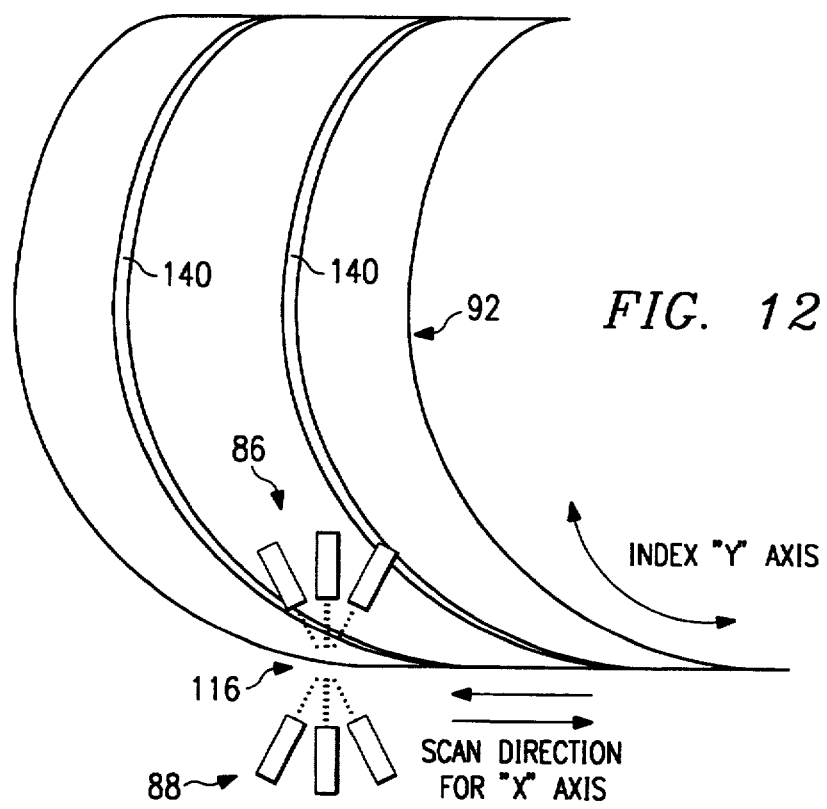
FIG. 12 is a simplified pictorial of the scanning method of the present invention.

FIG. 12 illustrates the method of inspecting a nacelle panel 92 using the present invention. The semi-automated system 10 will inspect the entire nacelle panel in one set of scan/index sequences controlled by the programmable controller 110 in one continuous operation in about one sixth the time of that necessary with prior art apparatus.

Figure 13A:
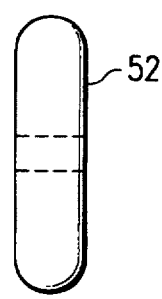
FIGS. 13a through 13e are simplified side elevational views showing exemplary wheels and rollers used in the present invention.
Figure 13B:
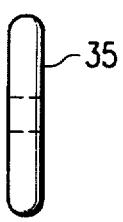
Figure 13C:
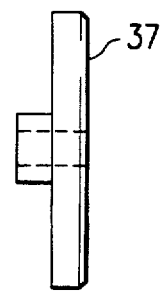
Figure 13D:
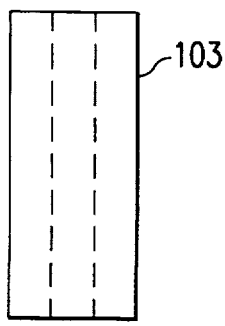
Figure 13E:
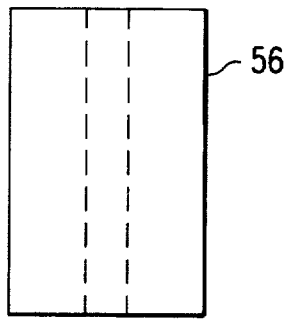

FIGS. 13a through 13e illustrate some exemplary wheels and rollers used in the preferred embodiment of the present invention. Lower wheel 52 is generally the same as lower wheel 54 and as shown in FIGS. 1, 2 and 4, supports the lower surface of the nacelle panel 92. Upper wheel 35, as shown in FIGS. 4 and 5, provides a downward force on the upper surface of the nacelle panel 92. Upper wheel 35 is used in conjunction with support wheel 37 when the nacelle panel 92 includes tabs which protrude from the edge or edges of the nacelle panel 92 and will be discussed further with respect to FIGS. 14 and 15a. One of the edge rollers 103 is illustrated in FIG. 13d, while one of the edge rollers 56 is illustrated in FIG. 13e, with each of these rollers being rotatable about a shaft indicated by the dashed lines in the respective figure.

Figure 14:
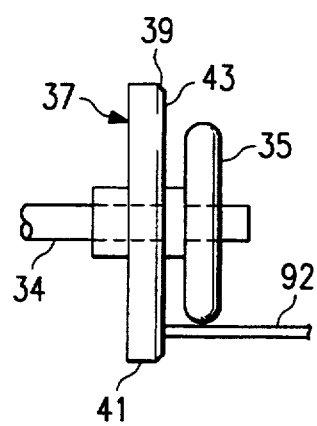
FIG. 14 is a simplified top plan view showing the operation of exemplary wheels with regard to a composite part having side tabs.

FIG. 14 illustrates the relationship of the upper wheel 35 and support wheel 37 in operative position with a nacelle panel 92 at a portion of the nacelle panel 92 which does not contain any tabs. Support wheel 37 includes a bevel portion 39 formed along one edge of the outer circumferentially extending surface 41 of the wheel. Upper wheel 35 and support wheel 37 are positioned on shaft 34 with upper wheel 35 being inboard of support wheel 37. The outer circumferentially extending surface of upper wheel 35 is in contact with the upper surface of nacelle panel 92 while the inside discoidal surface 43 of support wheel 37 is in contact with the edge surface of nacelle panel 92.

Figure 15A:
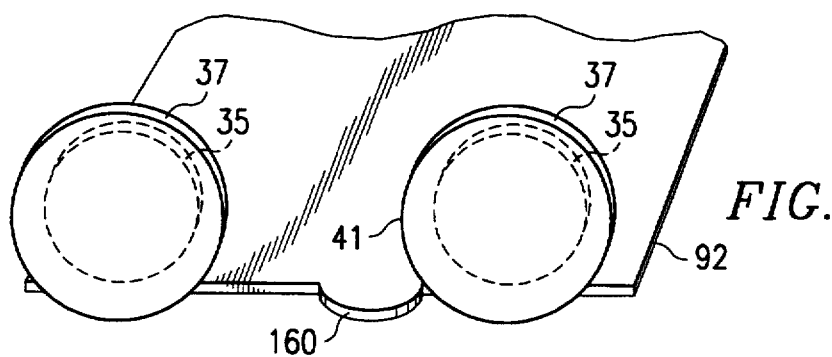
FIGS. 15a and 15b are simplified perspective views showing the operation of exemplary wheels and rollers with regard to a composite part having side tabs.

With reference to FIGS. 14 and 15a, there is shown a nacelle panel 92 in FIG. 15a with an exemplary tab 160 extending from the edge of the panel. As the nacelle panel 92 moves from left to right in FIG. 15a, the outer circumferentially extending surface 41 of support wheel 37 contacts the protruding tab 160 and rides upwardly onto the upper surface of tab 160 while the outer circumferentially extending surface of upper wheel 35 is lifted from contact with the nacelle panel 92. The other upper wheel 35 and support wheel 37 remain in contact with the nacelle panel 92 since they do not engage a tab and therefore maintain control of the nacelle panel 92.

Figure 15B:
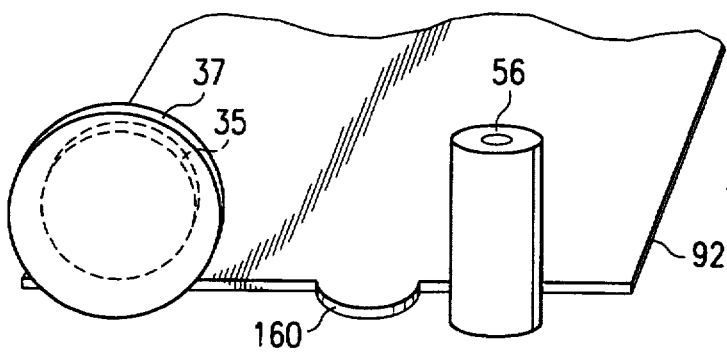

With reference to FIG. 15b, there is shown a nacelle panel 92 being supported and controlled by an upper wheel 35, a support wheel 37 and an edge roller 56. As tab 160 contacts edge roller 56, edge roller 56 moves outwardly while maintaining contact with the edge portion of tab 160 to maintain control of the nacelle panel 92 in conjunction with upper wheel 35 and support wheel 37.

In the operation of an ultrasonic inspection of a nacelle panel 92, the elements of the system are set up basically as depicted in FIGS. 4 and 5 with the addition of the two drive assemblies 122 mounted to the sides of tank 96 (see FIGS. 6 and 9). The nacelle panel 92 is positioned such that the leading edge is located in the inspection zone 116 with the wheels 35, 52 and 54 in operative position against the appropriate surfaces of nacelle panel 92. Electrical power is applied to appropriate equipment and the programmable controller 110 is activated which results in the upper and lower bridge assemblies 66 and 67 moving to the inspection zone 116 by operation of drive assembly 64. The upper and lower bridge assemblies 66 and 67 are scanned across the narrow width of the nacelle panel 92 along the "X" axis (which is parallel to the central upper and lower frames 22 and 62) in a direction from the second end frame assembly 16 toward the first end frame assembly 14 by drive assembly 64. At the completion of that scan, drive assembly 122 indexes the nacelle panel 92 a predetermined direction (determined by the programmable controller) in the "Y" direction along the longitudinal direction of the nacelle panel 92. Drive assembly 64 then scans the upper and lower bridge assemblies 66 and 67 across the narrow width of the nacelle panel 92 in a direction from the first end frame assembly 14 toward the second end frame assembly 16. It is appreciated that during the scanning operations that the ultrasonic transmitting and receiving transducer assemblies 86 and 88 are activated and the resulting received signals are coupled back to the video displays 112 and recorder 114. The scanning and indexing operations continue until the nacelle panel 92 is completely inspected or until the operator stops the inspection for some reason.

It will be appreciated that the present invention provides a system for ultrasonic inspection of a nacelle panel which moves the nacelle panel through an inspection zone by pulling the nacelle panel through the inspection zone by the use of cables removably attached to the nacelle panel. Instead of trying to control the ultrasonic transducers to maintain normality to the surface of the nacelle panel by either setting up small rectilinear scan zones or by use of some sort of contour control mechanism, the nacelle panel is controlled by applied force from wheels to maintain the nacelle panel flat within the inspection zone while the nacelle panel is being scanned. The semi-automated system can not only roll the nacelle panel through the inspection zone but by the use of shaped wheels the system can walk along external tabs of the nacelle panel and still maintain control of the movement of the nacelle panel.

Although the present invention has been described with reference to a presently preferred embodiment, it will be appreciated by those skilled in the art that various modifications, alternatives, variations, etc., may be made without departing from the spirit and scope of the invention as defined in the appended claims.

What is claimed is:

1. A method for nondestructive ultrasonic inspection of a curved composite panel for possible structural defects, said method comprising the steps of:

providing a first transducer carriage including at least one first ultrasonic transmitting transducer positioned on a first side of an inspection zone, wherein said first transducer carriage includes a second ultrasonic transmitting transducer oriented to transmit ultrasound at a predetermined angle between about plus forty to about plus fifty degrees with respect to the surface of the portion of the curved composite panel positioned in the inspection zone;

providing a second transducer carriage including at least one first ultrasonic receiving transducer positioned on a second side of the inspection zone;

supporting the curved composite panel for movement generally about the longitudinal axis of the curved composite panel;

transmitting ultrasound from the at least one first ultrasonic transmitting transducer and the second ultrasonic transmitting transducer through a liquid medium to the portion of the curved composite panel positioned in the inspection zone, through the curved composite panels and to the at least one first ultrasonic receiving transducer through a liquid medium;

moving the curved composite panel about its longitudinal axis in programmed index increments along the length of the curved composite panel and through the inspection zone;

moving the first and second transducer carriages in programmed scan increments across the width of the curved composite panel in the inspection zone after each programmed index increment; and analyzing the output of the at least one first ultrasonic receiving transducer to determine the presence of defects in the curved composite panel.

2. The method of claim 1 wherein said first transducer carriage includes a third ultrasonic transmitting transducer oriented to transmit ultrasound at a predetermined angle between about minus forty to about minus fifty degrees with respect to the surface of the portion of the curved composite panel positioned in the inspection zone.

3. The method of claim 2 wherein said second transducer carriage includes a second ultrasonic receiving transducer oriented to receive ultrasound at a predetermined angle between about minus forty to about minus fifty degrees with respect to the surface of the portion of the curved composite panel positioned in the inspection zone, and a third ultrasonic receiving transducer oriented to receive ultrasound at a predetermined angle between about plus forty to about plus fifty degrees with respect to the surface of the portion of the curved composite panel positioned in the inspection zone.

4. The method of claim 2 wherein said at least one first ultrasonic transmitting transducer includes at least one ultrasonic transmitting transducer oriented to transmit the ultrasound at generally ninety degrees to the surface of the portion of the curved composite panel positioned in the inspection zone.

5. The method of claim 4 wherein said second transducer carriage includes a second ultrasonic receiving transducer oriented to receive ultrasound at a predetermined angle between about minus forty to about minus fifty degrees with respect to the surface of the portion of the curved composite panel positioned in the inspection zone.

6. The method of claim 5 wherein said second transducer carriage includes a third ultrasonic receiving transducer oriented to receive ultrasound at a predetermined angle between about plus forty to about plus fifty degrees with respect to the surface of the portion of the curved composite panel positioned in the inspection zone.

7. The method of claim 6 wherein said at least one first ultrasonic receiving transducer includes at least one ultrasonic receiving transducer oriented to receive the ultrasound at generally ninety degrees to the surface of the portion of the curved composite panel positioned in the inspection zone.

8. The method of claim 1 wherein said at least one first ultrasonic transmitting transducer includes at least one ultrasonic transmitting transducer oriented to transmit the ultrasound at generally ninety degrees to the surface of the portion of the curved composite panel positioned in the inspection zone.

9. The method of claim 1 wherein said second transducer carriage includes a second ultrasonic receiving transducer oriented to receive ultrasound at a predetermined angle between about minus forty to about minus fifty degrees with respect to the surface of the portion of the curved composite panel positioned in the inspection zone.

10. The method of claim 9 wherein said at least one first ultrasonic transmitting transducer includes at least one ultrasonic transmitting transducer oriented to transmit the ultrasound at generally ninety degrees to the surface of the portion of the curved composite panel positioned in the inspection zone, and wherein said at least one first ultrasonic receiving transducer includes at least one ultrasonic receiving transducer oriented to receive the ultrasound at generally ninety degrees to the surface of the portion of the curved composite panel positioned in the inspection zone.

11. The method of claim 9 wherein said second transducer carriage includes a third ultrasonic receiving transducer oriented to receive ultrasound at a predetermined angle between about plus forty to about plus fifty degrees with respect to the surface of the portion of the curved composite panel positioned in the inspection zone.

12. A method for nondestructive ultrasonic inspection of a curved composite panel for possible structural defects, said method comprising the steps of:

providing a first transducer carriage including at least one first ultrasonic transmitting transducer positioned on a first side of an inspection zone;

providing a second transducer carriage including at least one first ultrasonic receiving transducer positioned on a second side of the inspection zone, wherein said second transducer carriage includes a second ultrasonic receiving transducer oriented to receive ultrasound at a predetermined angle between about minus forty to about minus fifty degrees with respect to the surface of the portion of the curved composite panel positioned in the inspection zone;

supporting the curved composite panel for movement generally about the longitudinal axis of the curved composite panel;

transmitting ultrasound from the at least one first ultrasonic transmitting transducer through a liquid medium to the curved composite panel positioned in the inspection zone, through the curved composite panel and to the at least one first ultrasonic receiving transducer and the second ultrasonic receiving transducer through a liquid medium;

moving the curved composite panel about its longitudinal axis in programmed index increments along the length of the curved composite panel and through the inspection zone;

moving the first and second transducer carriages in programmed scan increments across the width of the curved composite panel in the inspection zone after each programmed index increment; and analyzing the output of the at least one first ultrasonic receiving transducer and the second ultrasonic receiving transducer to determine the presence of defects in the curved composite panel.

13. The method of claim 12 wherein said second transducer carriage includes a third ultrasonic receiving transducer oriented to receive ultrasound at a predetermined angle between about plus forty to about plus fifty degrees with respect to the surface of the portion of the curved composite panel positioned in the inspection zone.

14. The method of claim 13 wherein said at least one first ultrasonic receiving transducer includes at least one ultrasonic receiving transducer oriented to receive the ultrasound at generally ninety degrees to the surface of the portion of the curved composite panel positioned in the inspection zone.

15. A method for nondestructive ultrasonic inspection of a curved composite panel for possible structural defects, said method comprising the steps of:
 providing a first transducer carriage including at least one ultrasonic transmitting transducer positioned on a first side of an inspection zone;
 providing a second transducer carriage including at least one ultrasonic receiving transducer positioned on a second side of the inspection zone;
 supporting the curved composite panel for movement generally about the longitudinal axis of the curved composite panel;
 transmitting ultrasound from the at least one ultrasonic transmitting transducer through a liquid medium to the curved composite panel positioned in the inspection zone, through the curved composite panel and to the at least one ultrasonic receiving transducer through a liquid medium;
 moving the curved composite panel about its longitudinal axis in programmed index increments along the length of the curved composite panel and through the inspection zone;
 moving the first and second transducer carriages in programmed scan increments across the width of the curved composite panel in the inspection zone after each programmed index increment; and
 analyzing the output of the at least one ultrasonic receiving transducer to determine the presence of defects in the curved composite panel;
 wherein said step of moving the curved composite panel about its longitudinal axis in programmed index increments is accomplished by the further steps of:
 providing a drive assembly operatively coupled to a cable retainer assembly having at least one cable therein;
 removably attaching said at least one cable to said curved composite panel; and
 activating said drive assembly from a programmable controller to move said curved composite panel through said inspection zone in said programmed index increments.

16. The method of claim 15 wherein said drive assembly comprises a stepper motor operatively coupled to an electronic position feedback device.

17. A method for nondestructive ultrasonic inspection of a curved composite panel for possible structural defects, said method comprising the steps of:
 providing a first transducer carriage including at least one ultrasonic transmitting transducer positioned on a first side of an inspection zone;
 providing a second transducer carriage including at least one ultrasonic receiving transducer positioned on a second side of the inspection zone;
 supporting the curved composite panel for movement generally about the longitudinal axis of the curved composite panel; wherein said first transducer carriage, said second transducer carriage, said inspection zone and the portion of the curved composite panel positioned in the inspection zone are immersed in a liquid medium contained in an immersion tank with a portion of the curved composite panel extending outside of and above the immersion tank;
 providing support to that portion of the curved composite panel extending outside of and above the immersion tank;
 transmitting ultrasound from the at least one ultrasonic transmitting transducer through said liquid medium to the curved composite panel positioned in the inspection zone, through the curved composite panel and to the at least one ultrasonic receiving transducer through said liquid medium;
 moving the curved composite panel about its longitudinal axis in programmed index increments along the length of the curved composite panel and through the inspection zone;
 moving the first and second transducer carriages in programmed scan increments across the width of the curved composite panel in the inspection zone after each programmed index increment; and
 analyzing the output of the at least one ultrasonic receiving transducer to determine the presence of defects in the curved composite panel.

18. The method of claim 17 wherein said support to that portion of the curved composite panel extending outside of and above the immersion tank is provided by rotatable guide wheels.

19. A method for nondestructive ultrasonic inspection of a curved composite panel for possible structural defects, said method comprising the steps of:
 providing a first transducer carriage including at least one ultrasonic transmitting transducer positioned on a first side of an inspection zone;
 providing a second transducer carriage including at least one ultrasonic receiving transducer positioned on a second side of the inspection zone;
 supporting the curved composite panel for movement generally about the longitudinal axis of the curved composite panel;
 transmitting ultrasound from the at least one ultrasonic transmitting transducer through a liquid medium to the curved composite panel positioned in the inspection zone, through the curved composite panel and to the at least one ultrasonic receiving transducer through a liquid medium;
 moving the curved composite panel about its longitudinal axis in programmed index increments along the length of the curved composite panel and through the inspection zone;
 providing support against the edge of said curved composite panel as said curved composite panel is moved through the inspection zone;
 moving the first and second transducer carriages in programmed scan increments across the width of the curved composite panel in the inspection zone after each programmed index increment; and
 analyzing the output of the at least one ultrasonic receiving transducer to determine the presence of defects in the curved composite panel;
 wherein said support against the edge of said curved composite panel is provided by rotatable guide rollers.

20. A semi-automated system for nondestructive ultrasonic inspection of a curved composite panel for detection of possible structural defects, said semi-automated system comprising:
 a first transducer carriage including at least one ultrasonic transmitting transducer positioned on a first side of an inspection zone;

a second transducer carriage including at least one ultrasonic receiving transducer positioned on a second side of the inspection zone; said first transducer carriage and said second transducer carriage constituting an ultrasonic inspection assembly;

means for supporting the curved composite panel as the curved composite panel is moved through the inspection zone;

means for providing a liquid medium between said at least one ultrasonic transmitting transducer and said inspection zone and between said at least one ultrasonic receiving transducer and said inspection zone, with the inspection zone being in the liquid medium;

means for moving the curved composite panel inspection zone in programmed index increments along the length of the curved composite panel while transmitting ultrasound from said at least one ultrasonic transmitting transducer through said liquid medium to the curved composite panel, through the curved composite panel and to said at least one ultrasonic receiving transducer through the liquid medium;

means for moving the ultrasonic inspection assembly in programmed scan increments across the width of the curved composite panel after each programmed index increment;

means for analyzing the output of the at least one ultrasonic receiving transducer to determine the presence of defects in the curved composite panel;

wherein said means for supporting comprises rotatable guide wheels in pressure contact with opposite sides of the curved composite panel and positioned on either side of the inspection zone to maintain the portion of the curved composite panel in the inspection zone generally normal to the signal from the at least one ultrasonic transmitting transducer.

21. The semi-automated system of claim 20 wherein said pressure contact of the rotatable guide wheels is provided by a regulated air pressure system.

22. The semi-automated system of claim 20 wherein said means for providing a liquid medium comprises an immersion tank for containing the liquid medium and adapted to receive a portion of the curved composite panel while another portion of the curved composite panel extends outside and above the immersion tank, and wherein the semi-automated system further includes rotatable guide wheels positioned outside and above the immersion tank and in contact with that portion of the curved composite panel extending outside the immersion tank.

23. The semi-automated system of claim 20 wherein said means for providing a liquid medium comprises a plurality of nozzles, each of said nozzles being associated with a respective one of said at least one ultrasonic transmitting transducer and said at least one ultrasonic receiving transducer for ejecting the liquid medium from the respective nozzle to said curved composite panel.

24. The semi-automated system of claim 20 wherein said means for providing a liquid medium comprises an immersion tank for containing a liquid medium to a predetermined depth.

25. A semi-automated system for nondestructive ultrasonic inspection of a curved composite panel for detection of possible structural defects, said semi-automated system comprising:

a first transducer carriage including at least one ultrasonic transmitting transducer positioned on a first side of an inspection zone;

a second transducer carriage including at least one ultrasonic receiving transducer positioned on a second side of the inspection zone; said first transducer carriage and said second transducer carriage constituting an ultrasonic inspection assembly;

means for supporting the curved composite panel as the curved composite panel is moved through the inspection zone;

means for providing a liquid medium between said at least one ultrasonic transmitting transducer and said inspection zone and between said at least one ultrasonic receiving transducer and said inspection zone;

means for moving the curved composite panel through the inspection zone in programmed index increments along the length of the curved composite panel while transmitting ultrasound from said at least one ultrasonic transmitting transducer through said liquid medium to the curved composite panel, through the curved composite panel and to said at least one ultrasonic receiving transducer through the liquid medium;

means for moving the ultrasonic inspection assembly in programmed scan increments across the width of the curved composite panel after each programmed index increment;

means for analyzing the output of the at least one ultrasonic receiving transducer to determine the presence of defects in the curved composite panel;

wherein said means for moving the curved composite panel through the inspection zone in programmed index increments comprises:

a drive assembly including a motor operatively coupled to an electronic position feedback device;

a programmable controller operatively coupled to said drive assembly;

a cable retainer assembly operatively coupled to said motor and structured to house at least one cable and extend the at least one cable from said cable retainer assembly and retrieve said at least one cable into said cable retainer assembly; and at least one cable housed within said cable retainer assembly which is removably attached to said curved composite panel such that said curved composite panel is pulled through the inspection zone in programmed index increments as the at least one cable is retrieved into said cable retainer assembly.

26. A semi-automated system for nondestructive ultrasonic inspection of a curved composite panel for detection of possible structural defects, said semi-automated system comprising:

a first transducer carriage including at least one ultrasonic transmitting transducer positioned on a first side of an inspection zone;

a second transducer carriage including at least one ultrasonic receiving transducer positioned on a second side of the inspection zone; said first transducer carriage and said second transducer carriage constituting an ultrasonic inspection assembly;

means for supporting the curved composite panel as the curved composite panel is moved through the inspection zone;

means for providing a liquid medium between said at least one ultrasonic transmitting transducer and said inspection zone and between said at least one ultrasonic receiving transducer and said inspection zone;

means for moving the curved composite panel through the inspection zone in programmed index increments along the length of the curved composite panel while transmitting ultrasound from said at least one ultrasonic transmitting transducer through said liquid medium to the curved composite panel, through the curved composite panel and to said at least one ultrasonic receiving transducer through the liquid medium;

means for moving the ultrasonic inspection assembly in programmed scan increments across the width of the curved composite panel after each programmed index increment;

means for analyzing the output of the at least one ultrasonic receiving transducer to determine the presence of defects in the curved composite panel;

wherein said means for moving the ultrasonic inspection assembly in programmed scan increments across the width of the curved composite panel comprises:

a drive assembly including a motor operatively coupled to an electronic position feedback device;

a programmable controller operatively coupled to said drive assembly;

a shaft and pulley means operatively coupled to said drive assembly;

a belt operatively coupled between said shaft and pulley means and said ultrasonic inspection assembly such that said ultrasonic inspection assembly is moved across the width of the curved composite panel after each programmed index increment.

27. Apparatus for pulling a curved composite panel through an inspection zone between an ultrasonic transmitting transducer and an ultrasonic receiving transducer of a nondestructive ultrasonic inspection system, said apparatus comprising:

means to support the curved composite panel as the curved composite panel is pulled through the inspection zone;

a drive assembly including a motor operatively coupled to an electronic position feedback device;

a cable retainer assembly operatively coupled to said motor and structured to house at least one cable and extend the at least one cable from said cable retainer assembly and retrieve said at least one cable into said cable retainer assembly; and at least one cable housed within said cable retainer assembly which is removably attached to said curved composite panel such that said curved composite panel is pulled through the inspection zone in programmed index increments as the at least one cable is retrieved into said cable retainer assembly.

28. The apparatus of claim 27 further including a programmable controller operatively coupled to said drive assembly.

29. Apparatus for controlling the orientation of a curved composite panel as the curved composite panel is moved through an inspection zone between a transmitting transducer and a receiving transducer of a nondestructive ultrasonic inspection system, said apparatus comprising:

a first plurality of rotatable guide wheels positioned on a first side of the inspection zone and in rolling pressure contact with a first side of the curved composite panel;

a second plurality of rotatable guide wheels positioned on a second side of the inspection zone and in rolling pressure contact with the first side of the curved composite panel;

a third plurality of rotatable guide wheels positioned on the first side of the inspection zone and in rolling pressure contact with a second side of the curved composite panel;

a fourth plurality of rotatable guide wheels positioned on the second side of the inspection zone and in rolling pressure contact with the second side of the curved composite panel;

means to maintain the rolling pressure contact of said first, second, third and fourth pluralities of rotatable guide wheels against said curved composite panel as the curved composite panel is moved through the inspection zone;

whereby the surface of the portion of the curved composite panel in the inspection zone is maintained generally normal to the orientation of the signal transmitted from the transmitting transducer to the receiving transducer in the inspection zone.

30. The apparatus of claim 27 wherein said rolling pressure contact of the first, second, third and fourth pluralities of rotatable guide wheels is provided by a regulated air pressure system.

31. The apparatus of claim 29 further including a fifth plurality of rotatable guide wheels positioned outboard from said third plurality of rotatable guide wheels and in rolling contact with said second side of said curved composite panel.

32. The apparatus of claim 31 further including a sixth plurality of rotatable guide wheels positioned outboard from said fourth plurality of rotatable guide wheels and in rolling contact with said second side of said curved composite panel.

33. The apparatus of claim 29 further including a first plurality of rotatable guide rollers positioned against a first edge of said curved composite panel.

34. The apparatus of claim 33 further including a second plurality of rotatable guide rollers positioned against a second edge of said curved composite panel.

35. Apparatus for controlling the orientation of a curved composite panel which includes external tabs which protrude outwardly from an edge of the curved composite panel as the curved composite panel is moved through an inspection zone between a transmitting transducer and a receiving transducer of a nondestructive ultrasonic inspection system, said apparatus comprising:

a first rotatable guide wheel and a second rotatable guide wheel positioned along a first edge portion of said curved composite panel and mounted on a first shaft, said first rotatable guide wheel having a first predetermined diameter, said second rotatable guide wheel having a second predetermined diameter which is smaller than said first predetermined diameter such that the circumferential surface of the second rotatable guide wheel is in rolling pressure contact with a first side of the curved composite panel and a side surface of said first rotatable guide wheel is in contact with the edge surface of said first edge portion of said curved composite panel;

a third rotatable guide wheel and a fourth rotatable guide wheel positioned along a second edge portion of said curved composite panel and mounted on a second shaft, said third rotatable guide wheel having a third predetermined diameter, said fourth rotatable guide wheel having a fourth predetermined diameter which is smaller than said third predetermined diameter such that the circumferential surface of the fourth rotatable guide wheel is in rolling pressure contact with the first side of the curved composite panel and a side surface of said third rotatable guide wheel is in contact with the edge surface of said second edge portion of said curved composite panel;

a first plurality of rotatable guide wheels in rolling pressure contact with a second side of the curved composite panel and positioned along the first edge portion; and a second plurality of rotatable guide wheels in rolling pressure contact with the second side of the curved composite panel and positioned along the second edge portion.

* * * * *

UNITED STATES PATENT AND TRADEMARK OFFICE
CERTIFICATE OF CORRECTION

PATENT NO. : 5,372,043
DATED : December 13, 1994
INVENTOR(S) : Speight, II et al It is certified that error appears in the above-indentified patent and that said Letters Patent is hereby corrected as shown below:

Column 9, line 3, delete "panels" and insert --panel--.

Column 13, line 15, after "panel" insert --through the--.

Column 16, line 23, delete "claim 27" and insert --claim 29--.

Signed and Sealed this

Seventh Day of March, 1995

Attest:

BRUCE LEHMAN

Attesting Officer

Commissioner of Patents and Trademarks